(12) United States Patent
Jacene et al.

(10) Patent No.: US 8,298,271 B2
(45) Date of Patent: Oct. 30, 2012

(54) INSTRUMENTS AND METHODS FOR HOLDING A BONE PLATE

(75) Inventors: Michael Jacene, Blackstone, MA (US); Jonathan Fanger, Raynham, MA (US); Eric Smith, North Attleboro, MA (US); Eric Kolb, Milton, MA (US)

(73) Assignee: DePuy Spine, Inc., Raynham, MA (US)

( * ) Notice: Subject to any disclaimer, the term of this patent is extended or adjusted under 35 U.S.C. 154(b) by 344 days.

(21) Appl. No.: 12/562,536

(22) Filed: Sep. 18, 2009

(65) Prior Publication Data
US 2010/0069967 A1 Mar. 18, 2010

Related U.S. Application Data

(62) Division of application No. 11/128,799, filed on May 13, 2005, now Pat. No. 7,604,638.

(60) Provisional application No. 60/581,692, filed on Jun. 21, 2004.

(51) Int. Cl.
*A61B 17/88* (2006.01)
(52) U.S. Cl. .............................. 606/281; 606/70; 606/71
(58) Field of Classification Search .................... 606/70, 606/71, 280–299
See application file for complete search history.

(56) References Cited

U.S. PATENT DOCUMENTS

| | | |
|---|---|---|
| 583,455 A | 6/1897 | Bush |
| 2,110,414 A | 3/1938 | Bell |
| 2,532,162 A | 11/1950 | Goss |
| 3,426,364 A | 2/1969 | Lumb |
| 4,096,857 A | 6/1978 | Cramer et al. |
| 4,201,215 A | 5/1980 | Crossett et al. |
| 4,269,180 A | 5/1981 | Dall |
| 4,289,123 A | 9/1981 | Dunn |
| 4,309,777 A | 1/1982 | Patil |
| 4,368,912 A | 1/1983 | Holtz |
| 4,401,112 A | 8/1983 | Rezaian |
| 4,657,550 A | 4/1987 | Daher |
| 4,743,260 A | 5/1988 | Burton |
| 4,759,769 A | 7/1988 | Hedman et al. |
| 4,904,263 A | 2/1990 | Buechel et al. |
| 4,932,975 A | 6/1990 | Main |
| 5,084,049 A | 1/1992 | Asher |
| 5,171,278 A | 12/1992 | Pisharodi |
| 5,236,460 A | 8/1993 | Barber |
| 5,246,458 A | 9/1993 | Graham |
| 5,352,225 A | 10/1994 | Yuan |
| 5,375,823 A | 12/1994 | Navas |
| 5,390,683 A | 2/1995 | Pisharodi |
| 5,423,826 A * | 6/1995 | Coates et al. ............... 606/96 |
| 5,458,641 A | 10/1995 | Ramirez Jimenez |
| 5,470,333 A | 11/1995 | Ray |
| 5,484,439 A | 1/1996 | Olson |
| 5,571,109 A | 11/1996 | Bertagnoli |
| 5,603,713 A | 2/1997 | Aust |
| 5,616,142 A | 4/1997 | Yuan |
| 5,653,763 A | 8/1997 | Errico |
| 5,672,175 A | 9/1997 | Martin |
| 5,672,177 A | 9/1997 | Seldin |
| 5,683,465 A | 11/1997 | Shinn |
| 5,693,100 A | 12/1997 | Pisharodi |
| 5,700,264 A | 12/1997 | Zucherman |
| 5,752,955 A | 5/1998 | Errico |

(Continued)

*Primary Examiner* — Thomas Barrett
*Assistant Examiner* — Melissa A Golob

(57) ABSTRACT

An instrument for insertion and placement of dynamic spinal fixation plates is provided. In general, the instrument is a clip that holds the plate at its maximum extension for implantation.

11 Claims, 7 Drawing Sheets

U.S. PATENT DOCUMENTS

| | | |
|---|---|---|
| 5,766,254 A | 6/1998 | Gelbard |
| 5,827,328 A | 10/1998 | Buttermann |
| 5,843,082 A | 12/1998 | Yuan |
| 5,865,846 A | 2/1999 | Bryan |
| 5,865,848 A | 2/1999 | Baker |
| 5,879,385 A | 3/1999 | Crockard |
| 5,885,284 A | 3/1999 | Errico |
| 5,902,304 A | 5/1999 | Walker |
| 5,916,267 A | 6/1999 | Tienboon |
| 5,941,881 A | 8/1999 | Barnes |
| 5,964,762 A | 10/1999 | Biedermann |
| 5,976,125 A | 11/1999 | Graham |
| 6,007,535 A | 12/1999 | Rayhack |
| 6,015,436 A | 1/2000 | Schonhoffer |
| 6,051,007 A | 4/2000 | Hogendijk |
| 6,066,142 A | 5/2000 | Serbousek |
| 6,080,193 A | 6/2000 | Hochshuler |
| 6,093,205 A | 7/2000 | McLeod |
| 6,102,950 A | 8/2000 | Vaccaro |
| 6,110,210 A | 8/2000 | Norton |
| 6,224,602 B1 | 5/2001 | Hayes |
| 6,235,034 B1 * | 5/2001 | Bray .................................. 606/71 |
| 6,238,396 B1 | 5/2001 | Lombardo |
| 6,258,125 B1 | 7/2001 | Paul |
| 6,306,136 B1 | 10/2001 | Baccelli |
| 6,328,738 B1 | 12/2001 | Suddaby |
| 6,402,756 B1 | 6/2002 | Ralph |
| 6,406,478 B1 | 6/2002 | Kuo |
| D460,184 S | 7/2002 | Schendel |
| 6,503,250 B2 | 1/2003 | Paul |
| 6,533,786 B1 | 3/2003 | Needham |
| 6,585,738 B1 | 7/2003 | Mangione |
| 6,645,208 B2 * | 11/2003 | Apfelbaum et al. ............ 606/71 |
| 6,652,525 B1 | 11/2003 | Assaker |
| 6,932,820 B2 | 8/2005 | Osman |
| 7,008,427 B2 | 3/2006 | Sevrain |
| 7,118,573 B2 | 10/2006 | Michelson |
| 7,186,254 B2 | 3/2007 | Dinh |
| 7,229,444 B2 | 6/2007 | Boyd |
| 7,604,638 B2 | 10/2009 | Jacene |
| 2002/0183754 A1 * | 12/2002 | Michelson ...................... 606/70 |
| 2003/0100902 A1 | 5/2003 | Wellisz |
| 2004/0019353 A1 | 1/2004 | Freid |
| 2004/0092939 A1 * | 5/2004 | Freid et al. ....................... 606/79 |
| 2004/0102773 A1 * | 5/2004 | Morrison et al. ................ 606/61 |
| 2004/0204710 A1 * | 10/2004 | Patel et al. ....................... 606/53 |
| 2004/0204712 A1 | 10/2004 | Kolb |
| 2005/0010227 A1 | 1/2005 | Paul |
| 2005/0049595 A1 | 3/2005 | Suh |
| 2005/0149026 A1 | 7/2005 | Butler |
| 2006/0116681 A1 | 6/2006 | Bert |
| 2007/0162021 A1 | 7/2007 | Dinh |

* cited by examiner

INSTRUMENTS AND METHODS FOR HOLDING A BONE PLATE

CROSS REFERENCE TO RELATED APPLICATIONS

This application is a divisional of U.S. patent application Ser. No. 11/128,799, filed May 13, 2005, which claims priority to U.S. Provisional Patent Application No. 60/581,692, filed Jun. 21, 2004, both of which are incorporated herein by reference.

FIELD

The present invention relates to instruments and methods for use with a spinal fixation plate, and in particular to instruments that can be used to extend a dynamic spinal fixation plate to an expanded configuration, for example, a fully extended configuration, to facilitate implantation.

BACKGROUND

Advancing age, as well as injury, can lead to changes in the bones, discs, joints, and ligaments of the spine, producing pain from nerve compression. Under certain circumstances, alleviation of pain can be provided by performing spinal fusion. Spinal fusion is a procedure that generally involves the removal of the disc between two or more adjacent vertebrae and the subsequent joining of the vertebrae with a bone fixation device to facilitate growth of new osseous tissue between the vertebrae. The new osseous tissue fuses the joined vertebrae such that the vertebrae are no longer able to move relative to each other. Bone fixation devices can stabilize and align the injured bone segments to ensure the proper growth of the new osseous tissue between the damaged segments. Bone fixation devices are also useful for promoting proper healing of injured or damaged vertebral bone segments caused by trauma, tumor growth, or degenerative disc disease.

One such bone fixation device is a bone fixation plate that is used to stabilize, align, and, in some cases, immobilize adjacent skeletal parts such as bones. Typically, the fixation plate is a rigid metal or polymeric plate positioned to span bones or bone segments that require stabilization, alignment, and/or immobilization with respect to one another. The plate may be fastened to the respective bones, usually with bone screws, so that the plate remains in contact with the bones and fixes them in a desired position. Bone plates can be useful in providing the mechanical support necessary to keep vertebrae in proper position and bridge a weakened or diseased area such as when a disc, vertebral body or fragment has been removed or during spinal fusion.

Such plates have been used to stabilize, align, and/or immobilize a variety of bones, including vertebrae of the spine. For example, a bone plate may include a plurality of screw openings, such as holes or slots, for screw placement. The bone plate may be placed against the damaged vertebrae and bone screws or other bone anchors can be used to secure the bone plate to the vertebrae. In the case of spinal fusion, for example, a prosthetic implant or bone graft may be positioned between the adjacent vertebrae to promote growth of osseous tissue and fusion of the vertebrae.

In spinal fusion procedures, conventional bone plates generally immobilize the connected vertebrae, imposing a rigid compressive load on the vertebrae. Gaps may develop in the new osseous tissue growing between the vertebrae, which can result in decoupling of the compressive load on the osseous tissue and the implant or graft positioned between the vertebrae. To address this problem, dynamic plates have been proposed that aim to permit the vertebrae to collapse axially during fusion. Examples of such dynamics plates are disclosed in commonly owned U.S. patent application Ser. No. 10/664,238, filed Sep. 17, 2003, entitled "Bone Fixation Plates," which is hereby incorporated by reference. Such exemplary dynamic plates are preferably implanted in the fully extended state. Manipulation of the plate during implantation can be challenging, as the segments of the plate may move relative to one another. There is a need for an instrument to assist in implanting dynamic plates in an extended state

SUMMARY

Disclosed herein are instruments and methods that facilitate the handling and insertion of dynamic spinal fixation plates to the bone portions to be stabilized, aligned, and/or immobilized.

In an exemplary embodiment of the present invention, an instrument for holding a plate having more than one segment has a first portion configured to hold a portion of a first segment of the plate and a second portion configured to fit between two adjacent segments of the plate to create a space therebetween.

An alternate embodiment of the present invention, an instrument for holding a plate includes a body portion with first and second ends, a handle extending from the body portion, an arm extending from the body portion to fit between adjacent plate segments and a leg extending from the body portion configured to attach to one segment of the plate.

In another embodiment of the present invention, the instrument has a pair of resilient legs biased in a closed position configured to expand to a second position to fit over a portion of a first segment of the plate and return to the first position to securely hold the first segment of the plate and an arm portion having a thickness configured to fit between adjacent segments of the plate to create a space therebetween.

Other embodiments provide features that will prevent accidentally leaving the instrument attached to the plate and implanted in the patient. This feature can be an extension of the leg such that when the clip is attached to the plate at least one screw hole is blocked by the leg preventing insertion of a bone screw. In another embodiment, this feature can be a tube projecting up from the legs. In yet another embodiment, the clip can be used with another style dynamic plate, which has a plurality of screw slots for placement of the screws and allows the screws to translate with respect to the plate. The clip covers a portion of each slot on the plate such that the screw can only be placed in one position in the slot. The clip directs the optimal placement of the screw within the slot.

The present invention also includes methods for using an instrument for implanting a plate having more than one segment. An exemplary method involves expanding the two segments of the plate to create a space therebetween, attaching the instrument to the plate between the segments, manipulating the instrument to position the plate into proximity with the bone while retaining the plate in the expanded state with the instrument, attaching at least one segment of the plate to the bone, and removing the instrument from the plate.

Another method for implanting a plate having first and second spaced apart screw slots for receiving a bone anchor involves positioning an instrument to obstruct a portion of the screw slots of at least one segment of said plate to bone, attaching the instrument to the plate to obstruct a portion of the first and second screw slots, attaching the plate to bone by placing a bone anchor through the unobstructed portion of each screw slot, and removing the instrument from the plate.

BRIEF DESCRIPTION OF THE DRAWINGS

The invention will be more fully understood from the following detailed description taken in conjunction with the accompanying drawings, in which.

DETAILED DESCRIPTION

The present invention provides instruments and methods for holding a dynamic multi-segment spinal fixation plate for proper implantation into bone. In general, the instrument has a first portion configured to hold a portion of a first segment of the plate and a second portion configured to fit between two adjacent segments of the plate to create a space therebetween. For ease of handling a handle may project from the body.

Figure 1:
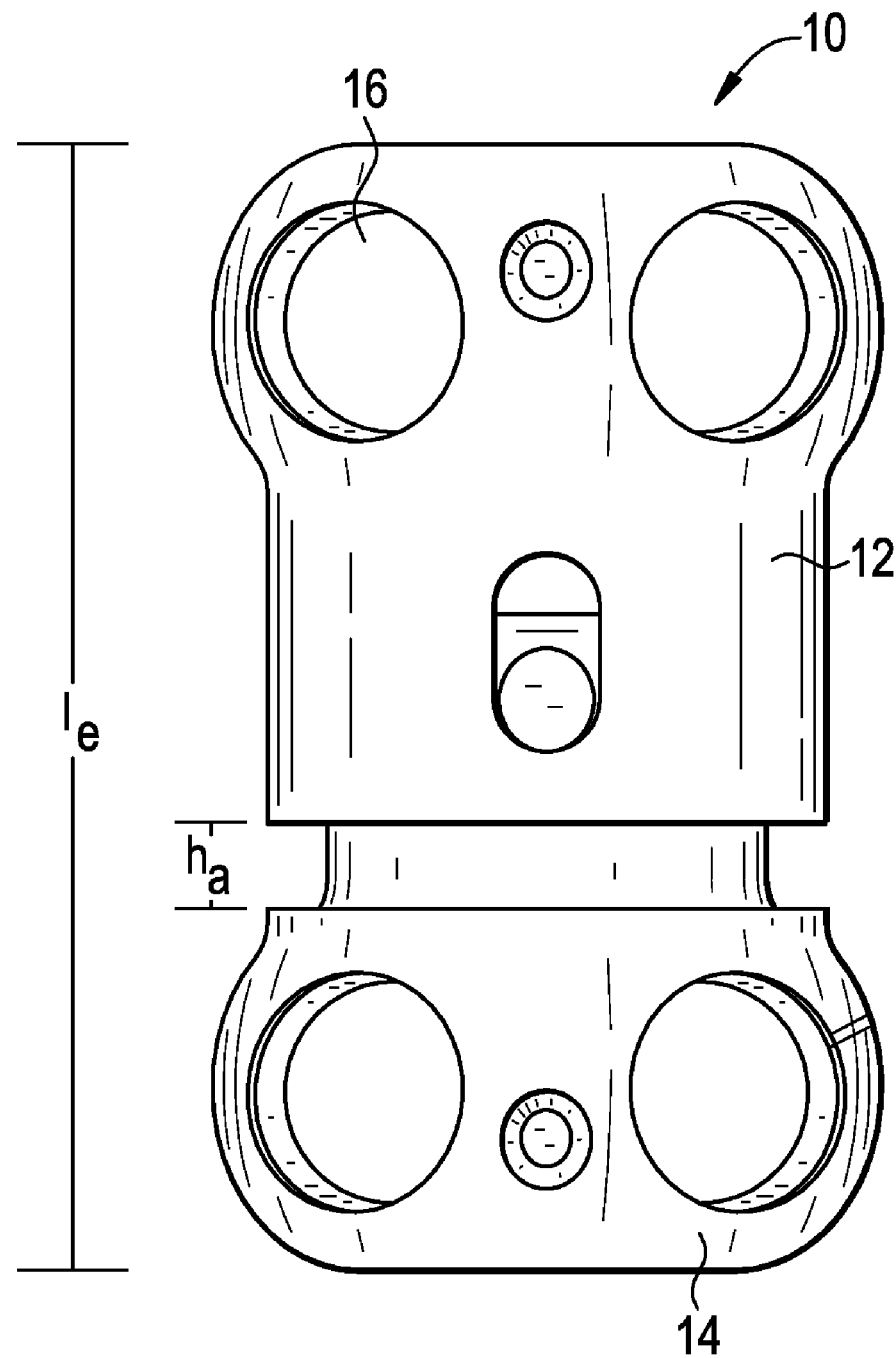
FIG. 1 is a top view of one embodiment of a multi-segmental dynamic spinal fixation plate in an expanded configuration, illustrating the plate in a fully extended state.
Figure 2A:
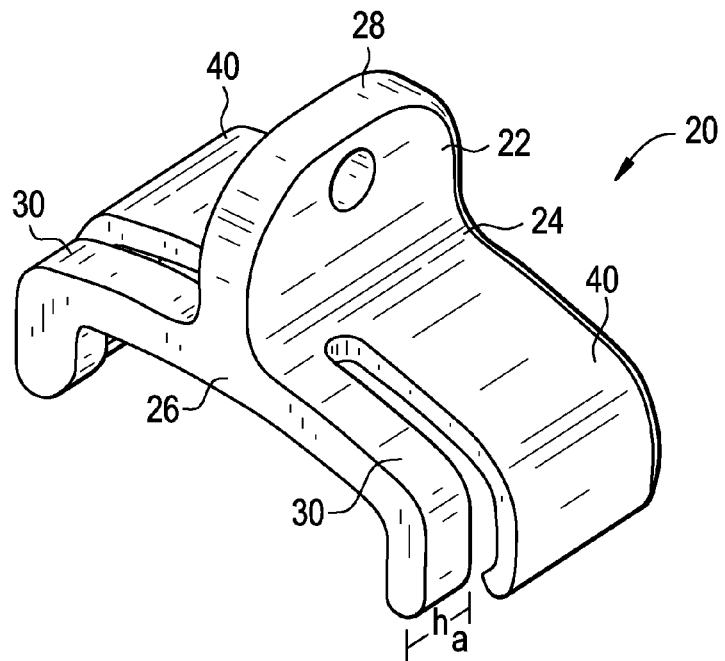
FIG. 2A is a top perspective view of one embodiment of the instrument of the present invention.

FIG. 1 illustrates one embodiment of a multi-segmental dynamic spinal fixation plate 10 which can be used in accordance with the present invention. As shown in FIG. 1, the plate 10 has two segments 12, 14 that move in relation to each other. Each segment has a least one screw hole 16. The plate 10, when implanted, is preferably positioned in an expanded state, for example, at its maximum length or expanded length. The present invention is directed to instruments and methods that facilitate implantation of a dynamic plate, such as the exemplary dynamic plate 10, in an expanded state. FIG. 2A shows an exemplary embodiment of the instrument 20 of the present invention. The instrument, referred to as an extension clip 20, has a body portion 22 having proximal 24 and distal 26 ends defining a longitudinal axis therebetween. A handle 28 projects from the body. The handle 28 aids in placing the clip 20 on the plate 10 and holding and manipulating the plate 10 during placement and attachment of the plate 10 to the bone. Arms 30 extend from opposite sides of the body portion 22 at the distal end 26 and legs 40 extend on opposite sides of the body portion 22 from the proximal end 40. The arms 30 have a height $h_a$ such that they fit between two segments 12, 14 of the fixation plate 10. Preferably, the height $h_a$ of the arms 30 is such that when the arms 30 are placed between the segments 12, 14 of the plate 10, the plate 10 is maintained in an expended state, for example, fully extended to its maximum length $l_e$. The height of the arms $h_a$ can be from 0.1 mm to 15 mm, preferably from 1 mm to 5 mm.

In the exemplary embodiment, the legs 40 of the clip 20 attach to one segment of a plate, for example, segment 12 of the exemplary plate 10. In one embodiment, such as the illustrated embodiment, the legs 40 of the clip 20 are resilient and biased towards a closed position. The legs 40 may be expanded to a second position to fit over a plate segment. Once released, the legs 40 returns to the original closed position and securely hold the plate segment. In other embodiments, the attachment can be a snap fit in which the legs 40 deform to fit around the plate segment. In alternative embodiments, the exemplary clip 20 may be connected to the plate by an adhesive, for example, provided on the undersurface of the legs 40 or other component of the clip 20 to allow the clip 10 to temporarily adhere to a plate segment. In alternative embodiments, the clip 20 may be attached to the plate 10 by a screw or tapered boss interacting with a bore in a plate segment. Preferably, the clip 20 is attached to the plate by an attachment mechanism, such as one of the mechanisms discussed above, that is sufficient to allow the plate 10 to be picked up and/or manipulated by the clip 20.

Figure 2B:
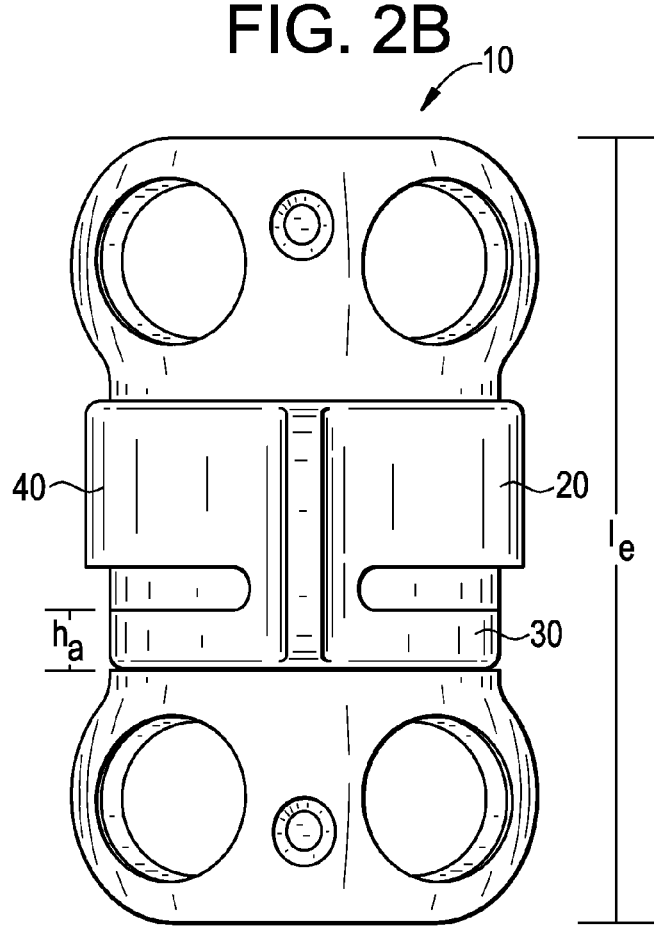
FIG. 2B is a top view of the spinal fixation plate in FIG. 1 with the instrument of FIG. 2A attached.

As shown in FIG. 2B, the exemplary clip 20 may be placed in position on the plate 10 with the arms 30 between the two plate segments 12, 14 and the legs 40 attached to one of the plate segments. As shown, with the exemplary clip 20 in place, the plate 10 is extended to an expanded state, for example, the plate's 10 maximum length $l_e$.

Figure 3A:
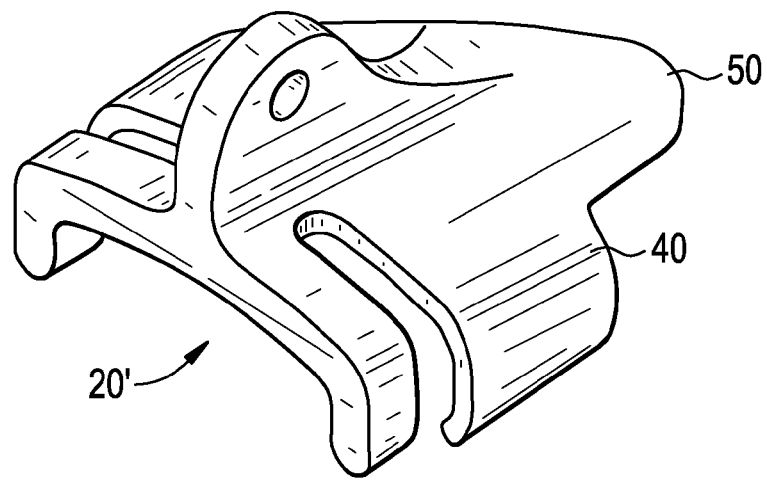
FIG. 3A is a top perspective view from the distal end of another embodiment of the present invention for holding a multi-segmental dynamic spinal fixation plate.
Figure 3B:
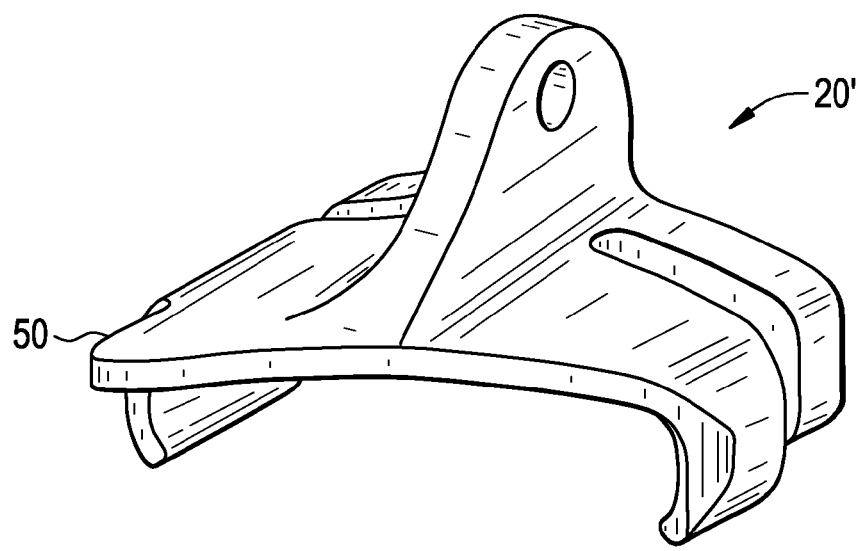
FIG. 3B is top perspective view from the distal end of the clip shown in FIG. 3A.
Figure 4A:
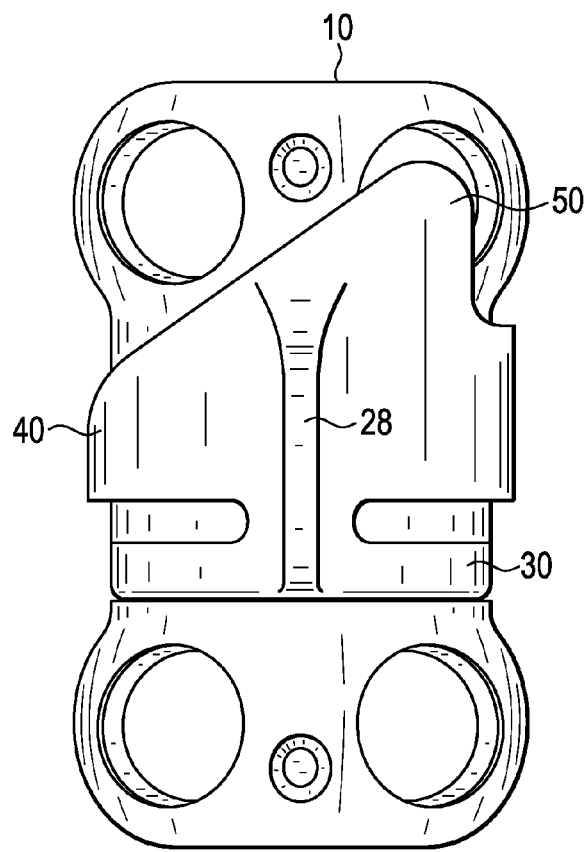
FIG. 4A is a top view of the spinal fixation plate shown in FIG. 1 with the instrument of FIG. 3A attached thereto.
Figure 4B:
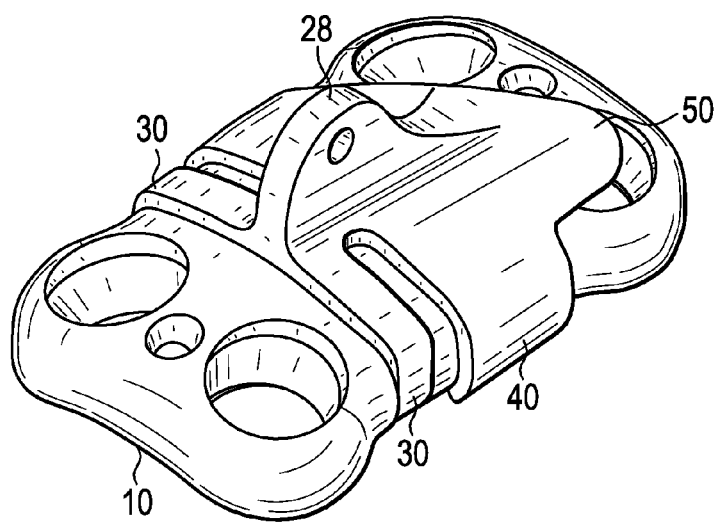
FIG. 4B is a top perspective view of the spinal fixation plate shown in FIG. 1 with the instrument of FIG. 3A attached thereto.

In an alternate embodiment, the clip can include a feature for minimizing the risk of accidentally leaving the clip attached to the plate at the conclusion of a surgical procedure. This feature can have many different forms. For example, an exemplary clip 20', illustrated in FIGS. 3A and 3B, is generally analogous in construction to the clip 20, discussed above, may include an extension 50 from one side of the legs 40 extending in a direction generally parallel to the longitudinal axis of the clip 20'. When the clip 20' is attached to the plate 10, the extension 50 is configured, e.g., has a size and shape, to at least partially block at least one of the screw holes 16 on the plate 10. As a result, the surgeon cannot insert a bone screw through the blocked or partially blocked hole to fully attach the plate to the bone without removing the clip 20' as illustrated in FIGS. 4A-4B. In addition, the clip may be impregnated with a radio opaque material, such as, for example, barium, or may include a maker that is visible through X-ray or other imaging.

Figure 5:
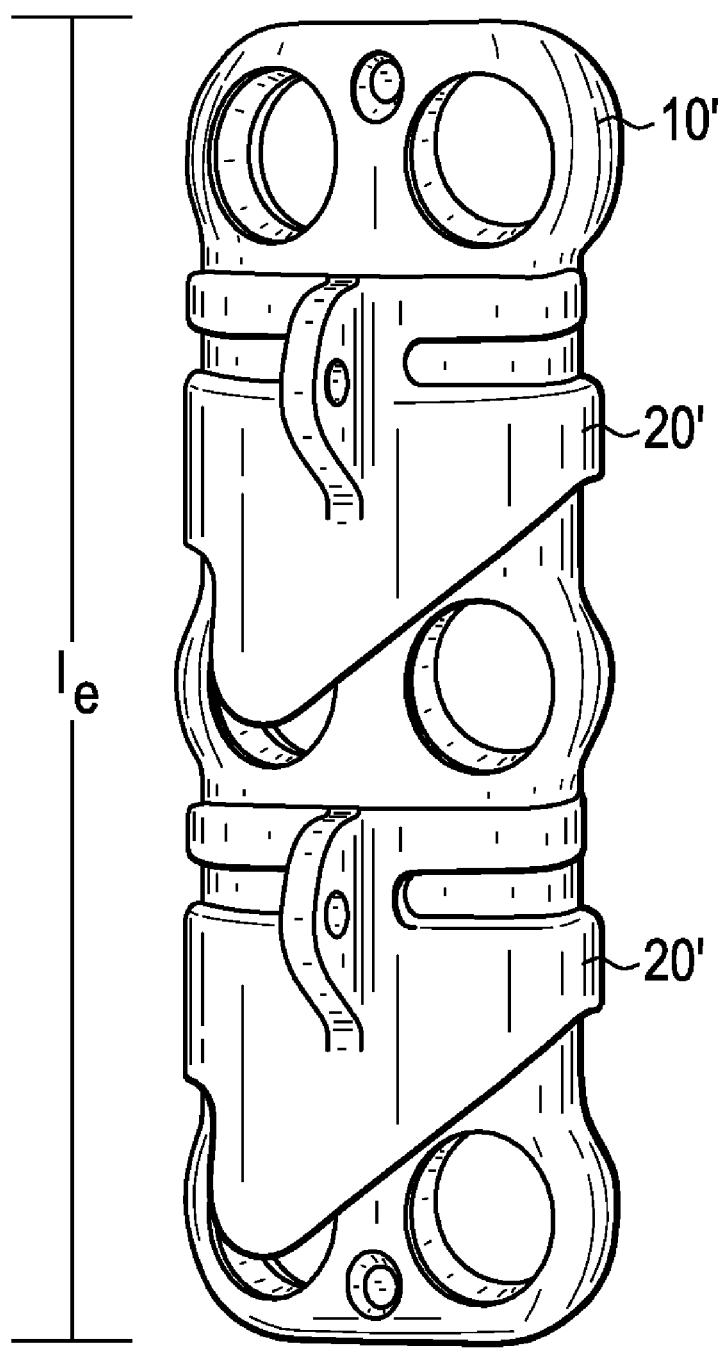
FIG. 5 is a top view of a multiple level dynamic spinal fixation plate with two of the instruments shown in FIG. 3A attached.

A person skilled in the art will appreciate that the plate 10 can include multiple segments. FIG. 5 illustrates a spinal fixation plate 10' that is substantially similar to plate 10, but that includes three segments to make up its overall length. By way of non-limiting example, two clips 20' can be used to hold this style plate in its fully extended position.

Figure 6:
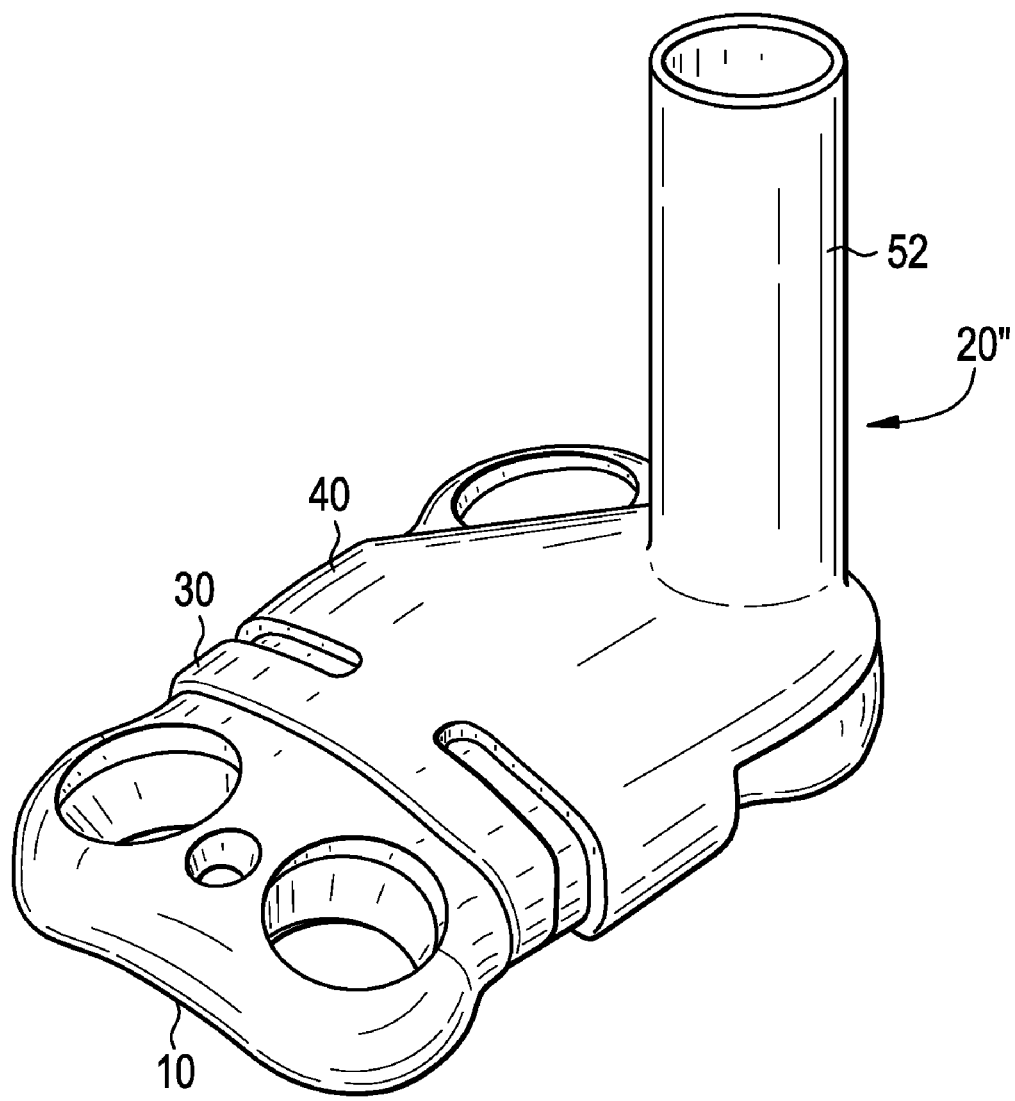
FIG. 6 is a top perspective view of yet another embodiment of the present invention having a drill guide formed integrally therewith.

Another embodiment of a clip 20" is shown in FIG. 6. The exemplary clip 20" may have an extension 50 from a leg 40 that includes a tube 52 projecting vertically from the plate 10. The tube 52 can be used as a drill guide so that the surgeon can drill through the tube 52 to prepare the bone for implanting the bone screw. In this exemplary embodiment, the leg extension 50 can also extend to partially block the opposite screw hole on the same plate segment.

Figure 7A:
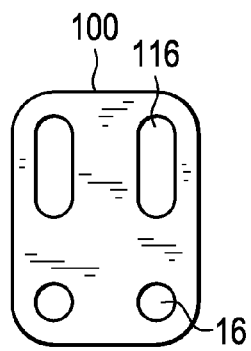
FIG. 7A is a top view of another style dynamic spinal fixation plate which allows the screws to translate within slots with respect to the plate.

An alternate embodiment of a dynamic spinal fixation plate 100 is shown in FIG. 7A. The exemplary plate 100, rather than having multiple segments to provide dynamism, instead includes screw holes 16 and screw slots 116 that allow the screws within the slots 116 to translate relative to the plate 100. The slots 116 are elongated, and, in the exemplary embodiment, have an elliptical, non-circular shape, although other shapes are possible. In the exemplary embodiment, the placement of a screw in relation to a slot 166 is important when implanting the plate 100. Optimal screw placement requires that the screws be placed at the maximum distance apart. Therefore, an instrument that can hold the plate and direct proper screw placement would be useful.

Figure 7B:
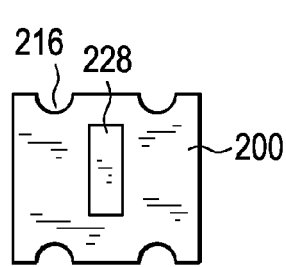
FIG. 7B is a top view of another embodiment of the present invention for use with the plate in FIG. 7A.
Figure 7C:
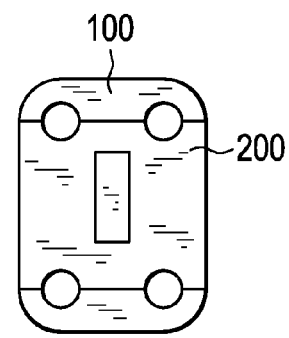
FIG. 7C is a top view of the plate with the instrument shown in FIG. 7B attached.
Figure 8A:
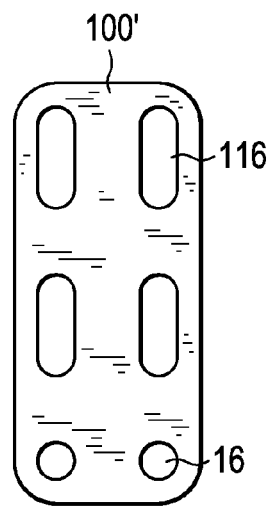
FIG. 8A is a top view of a multi-level dynamic spinal fixation plate.
Figure 8B:
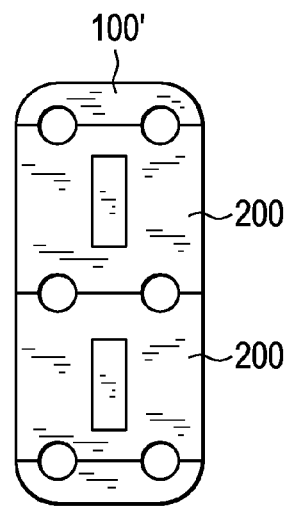
FIG. 8B is a top view of the plate shown in FIG. 8A with two instruments shown in FIG. 7B attached.

In another embodiment of the present invention, an exemplary clip 200 attaches to the plate 100 in the same manner as described above and has a handle 228 extending from the body of the clip 200 to facilitate handling of the plate 100 during insertion, as illustrated in FIGS. 7B and 7C. The exemplary clip 200 has a uniform body that covers a portion of the plate 100. The proximal and distal ends of the body of the clip 100 have semi-circular cutouts 216 that align over a portion of the screw slots 116 on the plate 100 to optimally direct the placement of the bone screws at the maximum distance apart. The screw slots 116 become screw holes 16 when the clip 200 is attached to the plate 100. A multilevel plate 100' is shown in FIG. 8A with screw holes 16 and screw slots 116. Two clips 200 can be used to implant this style plate as shown in FIG. 8B.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method of implanting a multi-segment spinal fixation plate including a first plate segment and an adjacent second plate segment movable relative to the first plate segment, the method comprising:
    separating a first portion of the first plate segment from a first portion of the second plate segment,
    attaching a first portion of an instrument to the first portion of the first plate segment, the first portion of the instrument having a pair of resilient legs biased in a closed position, the legs configured to expand to a second position to fit over the first portion of the first plate segment and return to the closed position to securely hold the first plate segment,
    positioning a second portion of an instrument between the first portion of the first plate segment and the first portion of the second plate segment, the second portion of the instrument having an arm with a thickness configured to fit between the first and second plate segments to create a space between the first and second plate segments,
    connecting the first plate segment to a first vertebra, and
    removing the instrument from the between the first portion of the first plate segment and the first portion of the second plate segment.

2. The method of claim 1, wherein connecting the first plate segment to the first vertebra includes positioning a bone anchor through a slot in the first plate segment and into the first vertebra.

3. The method of claim 1, further comprising connecting the second plate segment to a second vertebra.

4. The method of claim 3, wherein the instrument is removed before the second plate segment is connected to the second vertebra.

5. The method of claim 3, wherein the instrument is removed after the second plate segment is connected to the second vertebra.

6. The method of claim 3, wherein the first vertebra is adjacent the second vertebra.

7. The method of claim 1 further comprising positioning a first portion of the instrument over at least a portion of a top surface of a first plate segment of the plate while attaching the first portion to the first plate segment.

8. The method of claim 1, wherein the instrument further comprises a handle.

9. The method of claim 1, wherein the legs of the instrument extend to block a screw hole on at least one of the plate segments.

10. A method of implanting a multi-segment spinal fixation plate including a first plate segment and an adjacent second plate segment movable relative to the first plate segment, the method comprising:
    separating a first portion of the first plate segment from a first portion of the second plate segment,
    attaching a first portion of an instrument to the first portion of the first plate segment, the first portion of the instrument having a pair of resilient legs biased in a closed position, the legs configured to expand to a second position to fit over the first portion of the first plate segment and return to the closed position to securely hold the first plate segment, the first portion of the instrument obstructing a portion of a first screw hole in the first plate segment and preventing placement of a bone anchor through the obstructed first screw hole;
    positioning a second portion of an instrument between the first portion of the first plate segment and the first portion of the second plate segment, the second portion of the instrument having an arm with a thickness configured to fit between the first and second plate segments to create a space between the first and second plate segments,
    attaching the first plate segment to the bone by placing a bone anchor through a second screw hole in the first plate segment;
    removing the instrument from between the first portion of the first plate segment and the first portion of the second plate segment;
    placing a second bone anchor through the first screw hole.

11. A method of implanting a multi-segment spinal fixation plate including a first plate segment and an adjacent second plate segment movable relative to the first plate segment, the method comprising:
    separating a first portion of the first plate segment from a first portion of the second plate segment,
    attaching a first portion of an instrument to the first portion of the first plate segment, the first portion of the instrument having a pair of resilient legs biased in a closed position, the legs configured to expand to a second position to fit over the first portion of the first plate segment and return to the closed position to securely hold the first plate segment, the first portion of the instrument positioned to obstruct at least one screw hole on the first plate segment,
    positioning a second portion of an instrument between the first portion of the first plate segment and the first portion of the second plate segment, the second portion of the instrument having an arm with a thickness configured to fit between the first and second plate segments to create a space between the first and second plate segments,
    connecting the second plate segment to a first vertebra,
    removing the instrument from the between the first portion of the first plate segment and the first portion of the second plate segment, and
    connecting the first plate segment to a second vertebra.

* * * * *